Nov. 8, 1932. H. J. B. WIEDERKEHR Plant Pat. 42
GRAPE
Filed April 20, 1932
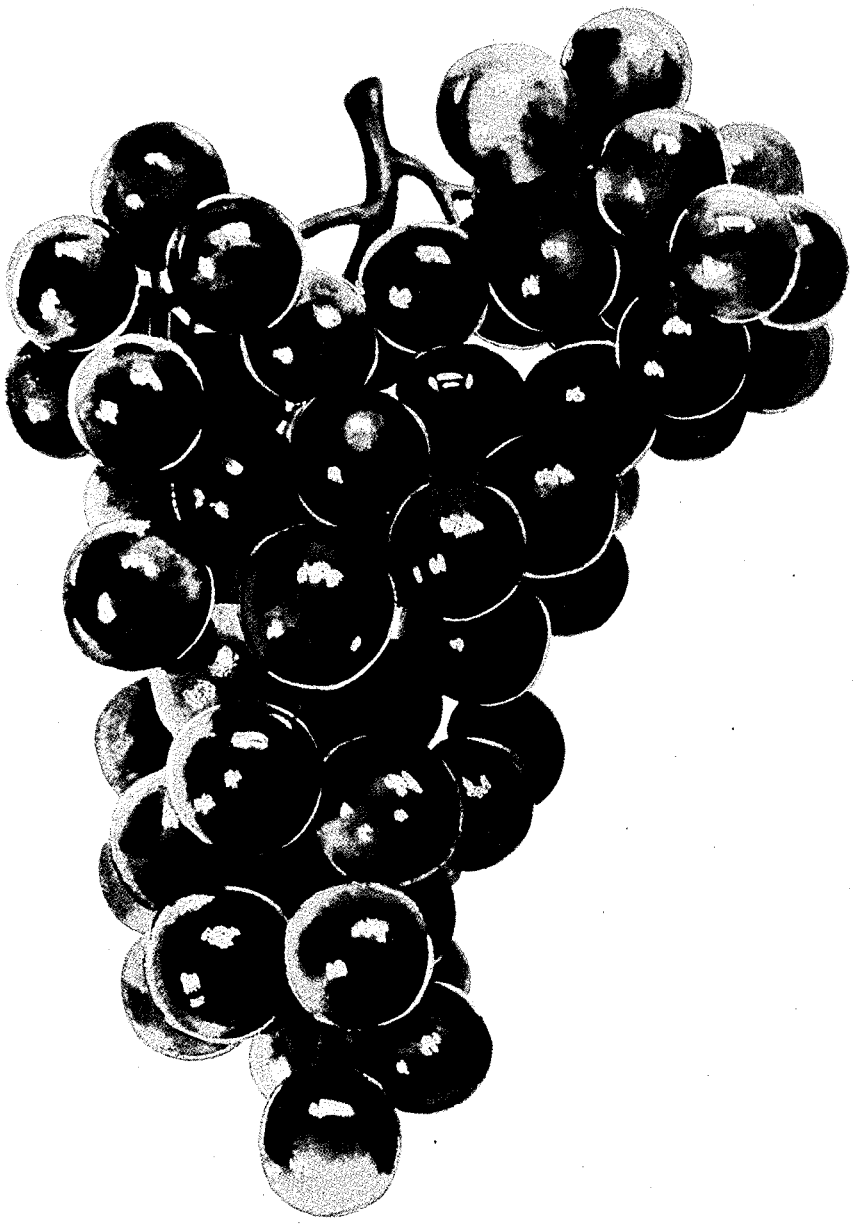
Inventor:
H. J. B. Wiederkehr
By Robb & Robb
Attorneys Patented Nov. 8, 1932

Plant Pat. 42

UNITED STATES PATENT OFFICE

HERMAN J. B. WIEDERKEHR, OF ALTUS, ARKANSAS, ASSIGNOR TO STARK BRO'S NURSERIES & ORCHARDS COMPANY, OF LOUISIANA, MISSOURI

GRAPE

Application filed April 20, 1932. Serial No. 606,485.

This invention relates to a new variety of grape of the so-called "black" grape class, the most outstanding and important characteristics of which reside in size and time of ripening.

From a commercial aspect or viewpoint, the relative times of ripening of various varieties of fruits is extremely important. This is best explained by reference to an illustrative example, and it is to be understood that it applies not only to grapes, but also to other fruits and plants in general productive of flowers or fruit requiring special handling or treatment. Take for example several varieties of grapes or other fruit which ripen at substantially the same time in a large vineyard or orchard. A large number of pickers are required to take care of the fruit at the proper time, thereby making it extremely difficult to utilize and save all of the fruit before it spoils. Likewise in the canning or other special treatments, considerable machinery and large forces for manning and operating the same are required, but for only the comparatively short ripening period. This represents a large capital outlay which is generally working and productive of returns only for a short time each season, depending upon the length of the ripening period. Thus, if the ripening periods of the various fruits could be spread over a longer time, considerable savings and increase in efficiency could be attained by the growers or producers and operators, resulting finally in lower cost of the final product, and increasing the quality incident to the increase in uniformity of production.

To this end, I have discovered and asexually reproduced my new variety of grape in that it increases the longevity of ripening season for grapes of the class to which it belongs.

The grape is one of the oldest of domesticated fruits and in the United States the black grapes are the great grapes of commerce. They are considered the best of all the grapes. In fact, the grape that made the grape industry in this country is the Concord. For many years, it has been the desire of the large grape grower to produce a grape of the Concord type which ripens in other seasons, and many efforts have been extended to this end for the purpose of lengthening the ripening and shipping season. Long after the introduction of the Concord, there was developed a variety called Campbell Early, ripening approximately fifteen days earlier than Concord when grown under comparable conditions. This variety averaged slightly larger than the Concord and proved to be a great commercial success.

My new grape is of the same type and has the same general appearance as the Campbell Early, but ripens approximately ten to fifteen days earlier, and twenty-five to thirty days earlier than Concord, thus providing a new season for a black grape. In size, my grape is considerably larger than either of the aforementioned or other varieties of this group and when grown under comparable conditions averages thirty to fifty per cent larger than Campbell Early. From an actual comparison of these grapes grown in the same vineyard and under comparable conditions, the individual fruit of the Campbell Early averaged one-half to nine-sixteenths of an inch in diameter whereas my individual fruit averaged three-quarters of an inch to one and one-eighth inches in diameter. In addition, the bunches of my new grape are much larger than Campbell Early or any other variety of black grape.

The quality of the fruit is far superior to that of Concord, Campbell Early, Moore's Early, Worden, Hicks, or any other black grape, being sweeter and more delicious in general. The Worden grape is the nearest approach in flavor.

Not only is the fruit entirely different from any other black grape, but the vine itself is distinct and easily distinguishable. The vines in the vineyard are very thrifty, and the foliage larger, darker, heavier and more leathery. In general, the foliage is unlike the foliage of any other American Grape and in both fruit and vine, the distinction is so plainly marked that even an inexperienced or layman observer can readily distinguish the difference from the varieties which most closely resemble my new variety. In fact, the differences are quite apparent even when observed from substantial distances away from the fruit and vines. Close and minute examination, of course, brings out numerous distinctions.

Having set forth the most notable features of my invention, it is apparent that my grape is clearly endowed with indivdual identity and is characterized truly as a new and distinct variety as manifested particularly in the earlier ripening of the fruit as compared with those varieties of the same class which most nearly resemble the same, the exceptionally large size of the individual fruit and bunches, the quality of the fruit, the individuality of foliage, and habit of growth. Certain of these features, especially the period of ripening, size, and quality of the fruit greatly enhance the value of the variety for commercial purposes.

What I claim as new is:—

A new and distinct variety of grape characterized particularly by the early ripening, exceptionally large size, and superior quality of its fruit, as herein shown and described.

In testimony whereof I affix my signature.

HERMAN J. B. WIEDERKEHR.